(12) United States Patent
Vaynberg

(10) Patent No.: US 7,973,004 B2
(45) Date of Patent: Jul. 5, 2011

(54) RHEOLOGY MODIFIER FOR AQUEOUS SURFACTANT-BASED FORMULATIONS

(75) Inventor: Konstantin A. Vaynberg, Cherry Hill, NJ (US)

(73) Assignee: Hercules Incorporated, Wilmington, DE (US)

( * ) Notice: Subject to any disclaimer, the term of this patent is extended or adjusted under 35 U.S.C. 154(b) by 0 days.

(21) Appl. No.: 12/704,799

(22) Filed: Feb. 12, 2010

(65) Prior Publication Data

US 2010/0204081 A1    Aug. 12, 2010

Related U.S. Application Data

(60) Provisional application No. 61/207,448, filed on Feb. 12, 2009.

(51) Int. Cl.
*C11D 3/37* (2006.01)
*C11D 1/00* (2006.01)
*C11D 7/10* (2006.01)
*A61K 8/91* (2006.01)

(52) U.S. Cl. ........ 510/475; 510/127; 510/351; 510/426; 510/492; 424/401; 424/486; 424/70.11; 424/70.21; 424/70.22

(58) Field of Classification Search .................. 510/127, 510/351, 426, 475, 492; 424/401, 486, 70.11, 424/70.21, 70.22
See application file for complete search history.

(56) References Cited

U.S. PATENT DOCUMENTS

| 5,574,127 | A | 11/1996 | Sau |
| 5,904,735 | A * | 5/1999 | Gutierrez et al. ................. 8/137 |
| 6,218,345 | B1 | 4/2001 | Brooks et al. |
| 7,550,542 | B2 | 6/2009 | Bakeev et al. |

FOREIGN PATENT DOCUMENTS

| EP | 0799887 B1 | 4/1996 |
| EP | 1876227 A1 | 7/2006 |
| WO | 2005077991 | 8/2005 |
| WO | 2007138053 | 12/2007 |
| WO | WO 2007/138053 | * 12/2007 |
| WO | WO 2008/146194 | * 12/2008 |

* cited by examiner

*Primary Examiner* — Brian P Mruk
(74) *Attorney, Agent, or Firm* — Robert O'Flynn O'Brien; Joanne Mary Fobare Rossi

(57) ABSTRACT

The present invention relates to aqueous formulations useful in useful in personal care, oral care, household and institutional applications which contain polymers comprised of water soluble synthetic backbone with covalently connected hydrophobic ends can deliver 'salt-like' rheology to surfactant formulations containing surfactant concentrations at which thickening by salt is not effective.

15 Claims, 1 Drawing Sheet

RHEOLOGY MODIFIER FOR AQUEOUS SURFACTANT-BASED FORMULATIONS

RELATED APPLICATIONS

This application claims the benefit of U.S. Provisional Application Ser. No. 61/207,448, filed on Feb. 12, 2009, the disclosure of which is incorporated herein by reference in its entirety.

FIELD OF INVENTION

The present invention relates to rheology modification of surfactant-based formulations for personal care, oral care, household and institutional applications such as hair care, skin care, household cleaners, wipes, and detergents.

BACKGROUND OF THE INVENTION

Viscosity control of formulations relating to various personal care, oral care, household and institutional applications in an important attribute for consumer use of such products.

Several approaches to control viscosity of such formulations are known to the art. Typically, a certain amount of a high molecular weight synthetic or natural polymers, such as, for example, linear or cross-linked acrylic acid based polymers, xanthan gum, various cellulose derivatives or other polysaccharide derivatives is incorporated into the formulation to impart a desired rheology.

Rheology delivered by these high molecular weight synthetic or natural polymers is usually strongly shear-thinning exhibiting high viscosity at low sheer rates, but relatively low viscosity at high shear. Such formulations usually do not exhibit a Newtonian or shear independent viscosity plateau, or if these formulation do exhibit Newtonian plateau, it is at shear rates below $1 \text{ s}^{-1}$.

A common and inexpensive method of delivering viscosity to formulations is through the addition of salts such as, for example, sodium chloride, sodium sulfate or ammonium chloride to the formulations. Addition of such salts in amounts ranging from between 0.1 to 5 wt % in cleansing formulations containing surfactants such as for example, sodium lauryl or ammonium lauryl sulfate, result in cleansing formulations with increased viscosity. One advantage of the use of salt to thicken formulations is that the resultant thickened cleansing formulation may be relatively clear.

Salt thickened formulations are commonly used and exhibit characteristic rheological properties. The characteristic rheological properties of these salt thickened formulations can be described as exhibiting shear independent (or Newtonian) viscosities up to a shear rate of the order of about 10 to $100 \text{ s}^{-1}$ followed by a decrease in its viscosity as the shear rate is increased above $100 \text{ s}^{-1}$. This phenomenon is known as "sheer-thinning". The salt thickening of formulations, however, has an important drawback in that the efficiency of salt to thicken a formulation decreases rapidly as the amount of surfactant contained in the formulation decreases.

A need exists for surfactant-based aqueous formulations exhibiting Newtonian viscosity at lower sheer rates and sheer thinning at higher sheer rates while permitting the use of various amounts of surfactants, including lower surfactant amounts.

SUMMARY OF THE INVENTION

Figure 1:
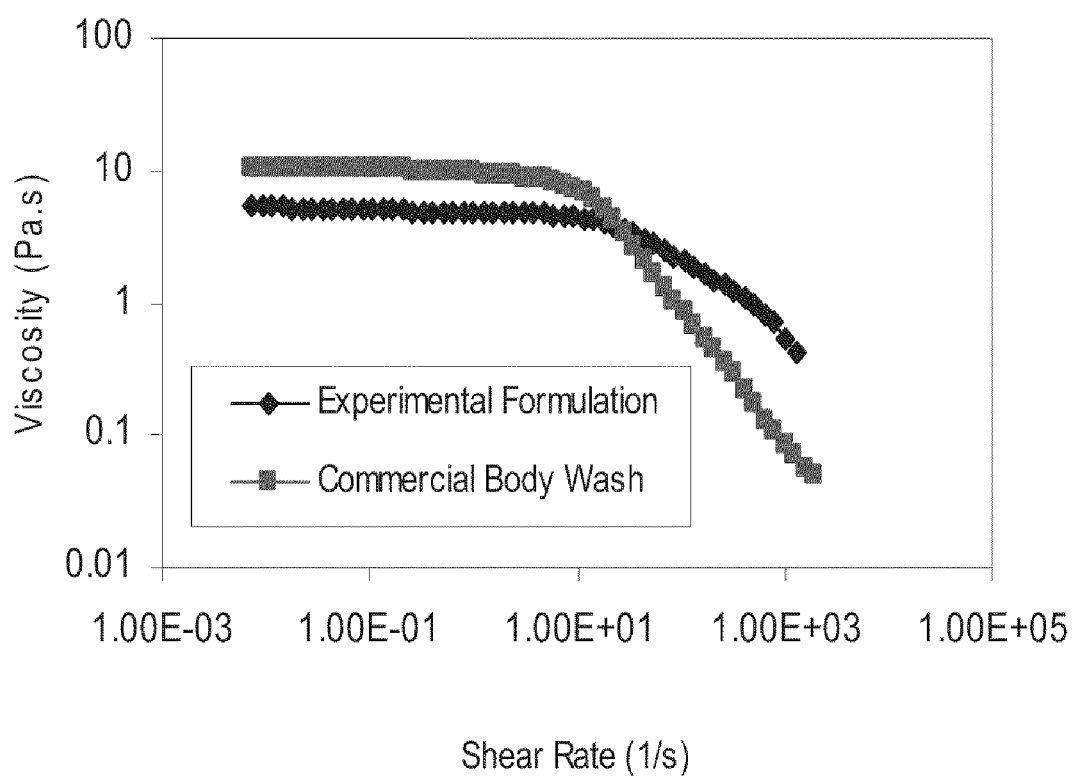
FIG. 1 is a graph of viscosity versus shear rate of a formulation of the present invention as well as, for comparison purposes, a conventional commercial bodywash formulation.

Applicant specifically incorporates the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It has been discovered that an aqueous formulation useful in personal care, oral care, household and institutional applications comprising: an amount of an associative thickener comprising a polymer composition having a water soluble or water-swellable synthetic polymer backbone that has covalently connected ends and/or intermediate blocks of oligomeric hydrophobes that are selected from the group consisting of i) alkyl and aryl moieties containing a polymerizable cyclic monomer, ii) a polymerizable double bond, and iii) derivatives of i) and ii), wherein the blocks are two or more units of the same or different hydrophobes. The aqueous formulation also comprises an amount of a surfactant and water. The amount of the associative thickener contained in the aqueous formulation is from about 0.1 to about 5 wt %, and the amount of surfactant contained in the aqueous formulation is from about 5 to about 50 wt %.

The thickening takes place within a continuum of an aqueous phase containing surfactant at a concentration in the range of from about 5 to about 50 wt % and does not require presence of any dispersed phases or interfaces.

DETAILED DESCRIPTION OF THE INVENTION

A rheology modifier, found to be effective in surfactant-based formulations, is an associative thickener based on hydrophilic core and associative hydrophobic ends. Rheology modifiers of this type have been used in thickening water-based coating formulations.

The rheology modifiers are known to lose their thickening efficiency in the presence of surfactants due to solubilization of their hydrophobic ends. While not wishing to be bound by theory, it is believed that solubilization of hydrophobic ends precludes these rheology modifiers from associating which in turn results in a decrease of their efficiency as rheology modifiers.

A negative impact of surfactants on the efficiency of associative thickeners is known in the field of water-based coatings. This negative impact manifests itself in the decrease of viscosity of paints upon addition of colorants, which often contain large concentrations of surfactants, to paint formulations.

There are, however, associative polymers with hydrophobes that are resistant to solubilization by commonly used surfactants. Such associative thickeners are described in U.S. Pat. No. 7,550,542, the disclosure of which is incorporated herein by reference in its entirety. A preferred associative polymer being an ethylhexyl glycidyl ether (EHGE) modified polyacetalpolyether (PAPE).

In accordance with the present invention, the associative polymer composition has a weight average molecular weight (Mw) with the upper limit of the polymer being about 10,000, 000, preferably about 1,000,000, and more preferably about 100,000. The lower limit of the weight average molecular weight of the polymer is about 400, preferably about 1,000, and more preferably about 4,000.

It has been found that associative thickeners described in U.S. Pat. No. 7,550,542 can be used as an effective rheology modifiers in surfactant-based formulations. The efficiency of these associative thickeners may be enhanced when used in conjunction with an amount of salt. The amount of salt contained in the formulations of the present invention is in the range of from about 0.1 to about 5 wt %. The salt can be any physiologically tolerated salt, e.g. sodium sulfate, potassium chloride or sodium chloride, preferably sodium chloride, in order to adjust the viscosity of the surfactant-based formulation.

Desired rheology modification is achieved at polymer concentrations at in the range of about 0.1 to about 5 wt % of the total formulation, preferably in the range of about 0.1 to about 3 wt %, still more preferably from about 0.2 to about 2 wt %. The obtained formulations exhibit broad Newtonian (i.e. shear independent) plateau followed by shear thinning at higher sheer rates.

The amount of surfactant contained in the formulations of the present invention is in the range of from about 5 to about 50 wt % of the total formulation, preferably from about 7 to about 48 wt %. The surfactant of use in the present formulation may be any surfactant commonly used in personal care, oral care, household and institutional applications. The surfactant may be selected from the group consisting of ammonium lauryl sulfate, sodium lauryl sulfate, ammonium laureth sulfate, sodium laureth sulfate and cocamidopropyl betaine.

In accordance with the present invention, the surfactant-based formulations may also include other active ingredients which typically are incorporated to provide some benefit to the user. Examples of substances that may suitably be included, but not limited to, according to the present invention are as follows:

1) Perfumes, which give rise to an olfactory response in the form of a fragrance and deodorant perfumes which in addition to providing a fragrance response can also reduce odor;

2) Insect repellent agent whose function is to keep insects from a particular area or attacking skin;

3) Bubble generating agent, such as surfactants which generates foam or lather;

4) Pet deodorizer such as pyrethrins which reduces pet odor;

5) Pet shampoo agents and actives, whose function is to remove dirt, foreign material and germs from the skin and hair surfaces and conditions the skin and hair;

6) Industrial grade bar, shower gel, and liquid soap actives that remove germs, dirt, grease and oil from skin, sanitizes skin, and conditions the skin;

7) All purpose cleaning agents, that remove dirt, oil, grease, germs from the surface in areas such as kitchens, bathroom, public facilities;

8) Disinfecting ingredients that kill or prevent growth of germs in a house or public facility;

9) Rug and Upholstery cleaning actives which lift and remove dirt and foreign particles from the surfaces and also deliver softening and perfumes;

10) Laundry softener actives which reduces static and makes fabric feel softer;

11) Laundry detergent ingredients which remove dirt, oil, grease, stains and kills germs;

12) Dishwashing detergents which remove stains, food, germs;

13) Toilet bowl cleaning agents which removes stains, kills germs, and deodorizes;

14) Laundry prespotter actives which helps in removing stains from clothes;

15) Fabric sizing agent which enhances appearance of the fabric;

17) Vehicle cleaning actives which removes dirt, grease, etc. from vehicles and equipment;

19) Textile products, such as dusting or disinfecting wipes.

Of particular interest are emollients selected from the group consisting of silicone oils, silicone derivatives, essential oils, oils, fats, fatty acids, fatty acid esters, fatty alcohols, waxes, polyols, hydrocarbons, and mixtures thereof. The emollients are stabilized by the use of associative polymers described hereinabove.

The above list of personal care and household active ingredients are only examples and are not a complete list of active ingredients that can be used. Other ingredients that are used in these types of products are well known in the industry.

The invention is further demonstrated by the following examples. The examples are presented to illustrate the invention. All percentages, parts and ratios are based upon the total weight of the compositions of the present invention, unless otherwise specified.

EXAMPLES

Example 1

Low Surfactant Formulation

A shampoo formulation was produced in which an associative thickener comprising a polymer composition having a water soluble or water swellable synthetic polymer backbone, ethylhexyl glycidyl ether modified polyacetalpolyether, Mw~10000 Dalton (Aquaflow® XLS 500 nonionic synthetic associative rheology modifier, available from Hercules Incorporated) was used as a rheology modifier for these shampoo formulations. This rheology modifier is described in U.S. Pat. No. 7,550,542.

The efficiency of this associative thickener as a rheology modifier in shampoo formulations was demonstrated using the following shampoo formulation: Sodium Laureth Sulfate SLES-7.7%, Cocamidopropyl betaine CAPB-1.3%, ethylhexyl glycidyl ether (EHGE) modified PAPE (Aquaflow® XLS 500 XLS 500 nonionic synthetic associative rheology modifier, available from Hercules Incorporated)-1%, NaCl-0.6%. The balance of the shampoo formulation being water. The above materials were combined using careful mixing. The rheology of the final shampoo formulation was determined using a Brookfield LVT viscometer, using a 4 spindle at 20° C.) temperature at various RPM to demonstrate the effect of sheer rate upon the shampoo formulation. No attempt was made to optimize the amount of rheology modifier or the amount of salt used in the shampoo formulation.

As can be seen in FIG. 1, the flow profile of the formulation of the present invention shows Newtonian plateau extending to the rate of 10 $s^{-1}$ followed by shear thinning. For comparison purposes, FIG. 1 also contains the flow profile of a commercial body wash formulation (High Endurance Body Wash by Old Spice, available from Proctor and Gamble) which exhibits profile similar to the formulation of the present invention but with slightly more sheer thinning at higher sheer rates.

The associative thickener as a rheology modifier in the shampoo formulation of the present invention demonstrated its effectiveness rheology modifier in the body wash/shampoo formulations having lower surfactant levels. Example 1 demonstrates rheological behavior of current cleansing systems at lower surfactant amounts.

Example 2

High Surfactant Formulation, without Silicone

A silicone-free cleansing formulation, which can be used for shampoo as well as body wash, comprising the nonionic synthetic associative thickener of Example 1 (Aquaflow® XLS 500 nonionic synthetic associative rheology modifier, available from Hercules Incorporated) was produced as described below. In each of the below listed Examples, a total of 0.20% w/w of the rheology modifier was used. This was an example of a silicone-free formulation.

In Example 2a, a solution comprising 25% of the nonionic synthetic associative rheology modifier of Example 1, 15% Iso-C10-Oxo-alcohol polyglycol ether (6 EO) and 60% water was produced.

In Example 2b, the associative thickener of Example 2a was used without the additional surfactant was produced.

In Comparative Example 2, a C12/C16 hydrophobically modified poly(acetal-polyether) Mw~24000 Dalton as disclosed in U.S. Pat. No. 5,574,127, was used. The disclosure of U.S. Pat. No. 5,574,127 is incorporated herein by reference in its entirety.

|  | Shampoo/Body Wash % W/W |
| --- | --- |
| Deionized water | 50.39 |
| PAPE polymer | 0.20 |
| Cocamidopropyl Betain (Tego ® betain L7, available from Evonik-Goldschmidt) | 7.41 |
| Sodium Laureth Sulfate (Texapon NSO, available from Cognis) | 40.00 |
| Phenoxyethanol, Ethylhexylglycerin (Euxyl ® PE 9010 preservative, available from Schülke & Mayr) | 0.50 |
| Sodium Chloride | 1.50 |
|  | 100 |
| Citric acid to pH 5.5-6.5 | q.s |

Reference shampoo contains no polymer.

The various shampoos are listed in Table 1.

The above samples all exhibited stability with a homogeneous appearance. Examples 2a and 2b both exhibited viscosities of 38,000 mPas and 32,500 mPas respectively which was approximately a six (6×) increase over Comparative Example 2, the shampoo composition containing the C12/C16 hydrophobically modified PAPE rheological modifier. Example 2 demonstrates the strong thickening efficiency of the EHGE modified PAPE in surfactant systems, with higher levels of surfactant than was used in Example 1.

Example 3

High Surfactant Formulation, with Silicone

In the same formulation of Example 2 with the addition of a silicone emulsion of dimethiconol (DC 1785 emulsion, available from Dow Corning Corporation) the associative thickeners of Example 3a and Example 3b provided improved stability (avoid destabilization of the silicone) over Comparative Example 3.

|  | Shampoo/Body Wash % W/W |
| --- | --- |
| Deionized water | 50.39 |
| PAPE polymer | 0.20 |
| Cocamidopropyl Betain (Tego ® betain L7, available from Evonik-Goldschmidt) | 7.41 |
| Sodium Laureth Sulfate (Texapon NSO, available from Cognis) | 40.00 |
| Dimethiconol, TEA-dodecylbenzenesulfonate (DC 1785 emulsion, available from Dow Corning Corporation) | 2.00 |
| Phenoxyethanol, Ethylhexylglycerin (Euxyl ® PE 9010 preservative, available from Schülke & Mayr) | 0.50 |
| Sodium Chloride | 1.50 |
|  | 100 |
| Citric acid to pH 5.5-6.5 | q.s |

Reference shampoo contains no polymer

TABLE 1

| Example | Info | Viscosity (Brookfield LVT, spindle # 4, speed 12 rpm) | pH | Appearance (after preparation) | Stability (Room Temp.) |
| --- | --- | --- | --- | --- | --- |
| Example 2 a1 | Ethylhexyl Glycidyl Ether (EHGE) modified PAPE + water/surfactant | 38000 mPas (~20x thickening vs. indication) | 5.9 | Homogeneous, clear | OK |
| Example 2b | Ethylhexyl Glycidyl Ether (EHGE) modified PAPE | 32500 mPas (~18x) | 5.7 | Homogeneous, slightly hazy | OK |
| Comp. Example 2 | C12/C16-PAPE | 5500 mPas (~3x) | 5.9 | Homogeneous, clear | OK |
| Shampoo | Blank | 1800 mPas | 6.3 | Homogeneous, clear | OK |

The various shampoos are listed in Table 2.

TABLE 2

| Example | Info | Viscosity (Brookfield LVT, spindle # 4, speed 12 rpm) | pH (after preparation) | Appearance | Stability (Room Temp., 1 month) |
|---|---|---|---|---|---|
| Example 3a | Ethylhexyl Glycidyl Ether (EHGE) modified PAPE + water/surfactant | 30750 mPas | 6.0 | Homogeneous, opaque | OK |
| Example 3b | Ethylhexyl Glycidyl Ether (EHGE) modified PAPE | 30500 mPas | 5.9 | Homogeneous, opaque | OK |
| Comp. Example 3 | C12/C16-PAPE | 5750 mPas | 5.9 | Homogeneous, opaque | After ~3 weeks separation, thin layer at the bottom |

The above Examples exhibited stability with a homogeneous appearance. Examples 3a and 3b both exhibited viscosities of 30,750 mPas and 30,500 mPas respectively which was approximately a six (6×) increase over Comparative Example 3, the shampoo composition containing the C12/C16 hydrophobically modified PAPE rheological modifier.

Example 4

High Surfactant Formulation, with Silicone

Using the same formulation as Example 3b with increased concentration of ethylhexyl glycidyl ether (EHGE) modified PAPE associative thickener, a sample formulation, as well as a comparative formulation, was prepared. The results of these formulations are found in Table 3

TABLE 3

| Example | Info | Percentage % wt | Viscosity (Brookfield LVT, spindle # 4, speed 12 rpm) | pH | Appearance (after preparation) | Stability (RT and 45° C.) 4 weeks |
|---|---|---|---|---|---|---|
| Example 4 | Ethylhexyl Glycidyl Ether (EHGE) modified PAPE | 3.0 | 16800 mPas (no salt) | 5.6 | Homogeneous, opaque, viscous liquid | RT: OK 45° C.: OK |
| Comp Example 4 | C12/C16-PAPE | 3.0 | 5,200 mPas (1.5% salt) | 6.0 | Homogeneous, opaque. | RT: after ~3 w slightly separation, thin layer at the bottom 45° C.: separation during the first week |

The formulation of Example 4 remained stable at 45° C. This demonstrates that the modified PAPE chemistry comprising the formulation of the present invention was able to deliver stabilization of silicone in a surfactant system whereas traditional alkyl end capped polyethylene glycols such as C12/C16 hydrophobically modified PAPE of Comparative Example 4 was not able to do this at even room temperature (25° C.). The stabilizing ability of oil emulsions in surfactant based formulations of the present invention was clearly demonstrated in Examples 3 and 4.

Example 5

Formulation at Low and High pH

In order to demonstrate the broad pH utility of an associative thickener comprising ethylhexyl glycidyl ether (EHGE) modified PAPE of Example 2b was tested in a shampoo body wash formulation with SLES/CAPB where the pH was adjusted to 3.7 with lactic acid and secondly to pH of 10 through sodium hydroxide.

| Shampoo formula adjusted to pH 3.7 | Shampoo/Body Wash % W/W |
|---|---|
| Deionized water | 50.39 |
| PAPE polymer | 0.20 |
| Cocamidopropyl Betaine (Tego ® betain L7, available from Evonik-Goldschmidt) | 7.41 |
| Sodium Laureth Sulfate (Texapon NSO, available from Cognis) | 40.00 |
| Phenoxyethanol, Ethylhexylglycerin (Euxyl ® PE 9010 preservative, available from Schülke & Mayr) | 0.50 |
| Sodium Chloride | 1.50 |
|  | 100 |
| Lactic acid to pH 3.7 | q.s |

| Shampoo formula adjusted to pH 10 | Shampoo/Body Wash % W/W |
|---|---|
| Deionized water | 50.39 |
| PAPE polymer | 0.20 |
| Cocamidopropyl Betain Tego ® betain L7, available from Evonik-Goldschmidt) | 7.41 |
| Sodium Laureth Sulfate (Texapon NSO, available from Cognis) | 40.00 |
| Phenoxyethanol, Ethylhexylglycerin (Euxyl ® PE 9010 preservative, available from Schülke & Mayr) | 0.50 |
| Sodium Chloride | 1.50 |
|  | 100 |
| NaOH to pH 10 | q.s |

TABLE 4

| Sample code | Associative Thickener | Percentage (% wt) | Viscosity (Brookfield LVT spindle # 4, speed 12 rpm) | pH | Stability (RT) |
|---|---|---|---|---|---|
| Example 5a | Ethylhexyl Glycidyl Ether (EHGE) modified PAPE | 1.50 | 4250 mPas | 3.7 | RT: OK Viscosity change <13.5% in 1 week |

TABLE 5

| Sample code | Associative Thickener | Percentage (%) | Viscosity (Brookfield LVT spindle # 4, speed 12 rpm) | pH | Stability (RT) |
|---|---|---|---|---|---|
| Example 5b) | Ethylhexyl Glycidyl Ether (EHGE) modified PAPE | 1.50 | 250 mPas | 10 | RT: OK Viscosity 39 mPas after 1 week, no phase separation |

The stability of the shampoo's at more extreme pH was observed to be OK. This can be observed above in Table 4 and Table 5. The viscosities were measured after one week at room temperature (25° C.). It was observed that the viscosity change was less than 10% at both the 3.7 pH formulation as well as the 10 pH formulation. This demonstrates that the formulations of the present invention are relatively stable over a wide range of pH values.

Example 6

Household Cleansing Formulation

Another example of a cleansing formulation is a household detergent with formulation given below:

|  | % W/W |
|---|---|
| Phase A - Floor cleaner concentrate |  |
| Water | 89.6 |
| EDTA, disodium salt | 0.17 |
| Alcohol Ethoxylate (9EO) | 10.26 |
| Phase B |  |
| Thickener 25% solution of ethylhexyl glycidyl ether modified polyacetalpolyether, Mw ~10000 Dalton (Aquaflow ® XLS 500 nonionic synthetic associative rheology modifier, available from Hercules Incorporated); 15% Iso-C10-Oxo-alcohol polyglycol ether (6 EO) | 1.0 |
| Water | 99.0 |

Combine ⅓ of Phase A to ⅔ of Phase B and mix well Viscosity can be adjusted by varying the amount of (EHGE) modified PAPE in phase B.

In the absence of additional salt (NaCl), the viscosity remained below 20 mPas at 1 wt % of polymer 1. With the addition of 4-8% sodium chloride, the viscosity of the cleaner could be increased to a range of 50 mPas (4% NaCl) and 450 mPas (8% NaCl). The cleaner without polymer and 8% NaCl had a viscosity of only 30 mPas. The viscosity was measured by Brookfield LVT 30 rpm, spindle #2.

Example 7

Conditioner Rinse Formula

A surfactant formulation of use in a conditioner rinse containing the (EHGE) modified PAPE of Example 2b is given below:

|  | % W/W |
|---|---|
| Deionized water | q.s. to 100 |
| (EHGE) modified PAPE | 1.00 |
| Centrimonium chloride | 1.00 |
| Ceteareth-20 | 0.50 |
| Ceateryl Alcohol | 4.00 |
| Amodimethicone | 1.00 |
| Phenoxyethanol, Ethylhexylglycerin (Euxyl ® PE 9010 preservative, available from Schülke & Mayr) | 0.50 |
| Sodium Lactate/Lactic Acid | q.s. |

The end pH: 5.5-6.5

Examples 6 and 7 demonstrate the utility of (EHGE) modified PAPE I various aqueous formulations such as household cleaning formulations and conditioner rinse formulations.

Although the invention has been illustrated by the above examples, this is not to be construed as being limited thereby; but rather, the invention encompasses the generic area as hereinbefore disclosed. Various modifications and embodiments can be made without departing from the spirit and scope of the invention.

What is claimed:

1. An aqueous formulation useful in personal care, household and institutional applications comprising:
   a. an amount of an associative thickener comprising a polymer composition having a water soluble or water swellable synthetic polymer backbone that has covalently connected ends and/or intermediate blocks of oligomeric hydrophobes that are selected from the group consisting of i) alkyl and aryl moieties containing a polymerizable cyclic monomer, ii) a polymerizable double bond, and iii) derivatives of i) and ii), wherein the blocks are two or more units of the same or different hydrophobes;
   b. and amount of a surfactant; and
   c. water;
   wherein the amount of the associative thickener contained in the aqueous formulation is from about 0.1 to about 5 wt %, and the amount of surfactant contained in the aqueous formulation is from about 5 to about 50 wt %, and wherein the polymer composition having a water soluble or water swellable synthetic polymer backbone further comprises an ethylhexyl glycidyl ether (EHGE) modified polyacetalpolyether.

2. The aqueous formulation of claim 1, further comprising an amount of a physiologically tolerated salt selected from the group consisting of sodium sulfate, potassium chloride and sodium chloride, wherein the amount of salt contained in the aqueous formulation is from about 0.1 to about 5 wt %.

3. The aqueous formulation of claim 2, wherein the physiologically tolerated salt comprises sodium chloride.

4. The aqueous formulation of claim 1, wherein the amount of the associative thickener contained in the aqueous formulation is in the range of about 0.1 to about 3 wt %.

5. The aqueous formulation of claim 4, wherein the amount of the associative thickener contained in the aqueous formulation is in the range of about 0.2 to about 2 wt %.

6. The aqueous formulation of claim 1, wherein the amount of the surfactant contained in the aqueous formulation is from about 7 to about 48 wt %.

7. The aqueous formulation of claim 1, the polymer composition having a water soluble or water swellable synthetic polymer backbone has a weight average molecular weight (Mw) with the upper limit of the polymer being about 10,000,000.

8. The aqueous formulation of claim 7, wherein the polymer composition having a water soluble or water swellable synthetic polymer backbone has a weight average molecular weight (Mw) with the upper limit of the polymer being about 1,000,000.

9. The aqueous formulation of claim 8, wherein the polymer composition having a water soluble or water swellable synthetic polymer backbone has a weight average molecular weight (Mw) with the upper limit of the polymer being about 100,000.

10. The aqueous formulation of claim 7, wherein the polymer composition having a water soluble or water swellable synthetic polymer backbone has a weight average molecular weight (Mw) with the lower limit of about 400.

11. The aqueous formulation of claim 10, wherein the polymer composition having a water soluble or water swellable synthetic polymer backbone has a weight average molecular weight (Mw) with the lower limit of about 1,000.

12. The aqueous formulation of claim 11, wherein the polymer composition having a water soluble or water swellable synthetic polymer backbone has a weight average molecular weight (Mw) with the lower limit of about 4,000.

13. The aqueous formulation of claim 1, wherein the surfactant is selected from the group consisting of ammonium lauryl sulfate, sodium lauryl sulfate, ammonium laureth sulfate, sodium laureth sulfate and cocamidopropyl betaine.

14. The aqueous formulation of claim 1, further comprising an amount of an emollient selected from the group consisting of silicone oils, silicone derivatives, essential oils, oils, fats, fatty acids, fatty acid esters, fatty alcohols, waxes, polyols, hydrocarbons, and mixtures thereof.

15. The aqueous formulation of claim 14, wherein the emollient comprises silicone oil.

* * * * *